(12) United States Patent
Hotier et al.

(10) Patent No.: US 8,030,533 B2
(45) Date of Patent: Oct. 4, 2011

(54) METHOD FOR COMBINED PRODUCTION OF PARAXYLENE AND BENZENE WITH IMPROVED PRODUCTIVITY

(75) Inventors: Gerard Hotier, Rueil Malmaison Cedex (FR); Kim Seo Il, Ulsan-si (KR)

(73) Assignee: IFP Energies Nouvelles, Rueil-Malmaison Cedex (FR)

(*) Notice: Subject to any disclaimer, the term of this patent is extended or adjusted under 35 U.S.C. 154(b) by 657 days.

(21) Appl. No.: 11/908,704

(22) PCT Filed: Mar. 14, 2006

(86) PCT No.: PCT/FR2006/000557
§ 371 (c)(1), (2), (4) Date: Oct. 16, 2008

(87) PCT Pub. No.: WO2006/097618
PCT Pub. Date: Sep. 21, 2006

(65) Prior Publication Data
US 2009/0069612 A1    Mar. 12, 2009

(30) Foreign Application Priority Data

Mar. 16, 2005    (FR) ...................... 05 02621

(51) Int. Cl.
*C07C 4/24*    (2006.01)
*C07C 7/12*    (2006.01)
*C07C 7/14*    (2006.01)
(52) U.S. Cl. ........ 585/470; 585/820; 585/828; 585/812; 585/814
(58) Field of Classification Search .................. None
See application file for complete search history.

(56) References Cited

U.S. PATENT DOCUMENTS

| 3,699,181 A * | 10/1972 | Kmecak et al. ............... 585/321 |
| 3,813,452 A * | 5/1974 | Bieser ........................... 585/479 |
| 5,401,476 A | 3/1995 | Hotier et al. |
| 5,629,467 A * | 5/1997 | Hotier et al. .................. 585/805 |
| 5,866,740 A | 2/1999 | Mikitenko et al. |
| 6,004,452 A | 12/1999 | Ash et al. |
| 2009/0234170 A1 * | 9/2009 | Lee et al. ...................... 585/470 |
| 2010/0105971 A1 * | 4/2010 | Lee et al. ...................... 585/323 |

* cited by examiner

Primary Examiner — Tam M Nguyen
(74) Attorney, Agent, or Firm — Millen, White, Zelano & Branigan, P.C.

(57) ABSTRACT

A process for the combined production of para-xylene and benzene comprises:
  separating a first feed, by adsorption in a simulated moving bed SMB, to produce an extract E rich in para-xylene and at least one raffinate R which is depleted in para-xylene;
  converting a secondary feed of toluene by selective disproportionation to produce benzene and xylenes;
a) at the start of the cycle, producing a supplemental quantity of para-xylene in a crystallization unit supplied with the xylenes from the disproportionation;
b) at the end of the cycle, when the adsorbant has aged:
  dividing the distilled extract E into a first fraction Ea and a complementary second fraction Eb;
  replacing the feed to the initial crystallization by the stream Ea;
  and recycling the xylenes from the disproportionation to the SMB.

The invention enables para-xylene and benzene production to be maintained despite ageing of the SMB absorbent.

15 Claims, 2 Drawing Sheets

METHOD FOR COMBINED PRODUCTION OF PARAXYLENE AND BENZENE WITH IMPROVED PRODUCTIVITY

FIELD OF THE INVENTION

Global production of para-xylene has been increasing steadily for thirty years by an annual average of 5% to 6%. Conventional uses of para-xylene (PX) are the production of terephthalic acid, phthalic anhydride and terephthalate polyethylene resins to provide synthetic textiles, audio and video cassettes and, more generally, plastics materials. Benzene is another intermediate in petrochemistry which has many uses, for example the production of straight chain alkylbenzenes used in washing powder, the production of cyclohexane, etc. The invention relates to an improved process for the combined production of para-xylene and benzene from a first aromatic feed comprising xylenes and from a second feed of toluene.

PRIOR ART

Para-xylene (PX) is typically present in $C_8$ aromatic cuts (containing 8 carbon atoms) from catalytic reforming and/or from steam cracking. "Para-xylene production" means separating high purity para-xylene, over 99%, for example at least 99.7% by weight, from such a complex $C_8$ hydrocarbon cut, possibly comprising minor quantities of aromatic $C_7$ and/or $C_9$ hydrocarbons and small quantities of non aromatic hydrocarbons, for example $C_8$ naphthenes.

Two processes or additional process steps are known which can increase the quantity of para-xylene initially comprised in an aromatic cut:

a) isomerization, typically converting ortho-xylene and meta-xylene into a mixture of xylenes close to thermodynamic equilibrium. Preferably, an isomerization which also transforms ethylbenzene is used. The prior art already contains two principal types of said isomerization:

"converting" isomerization which also transforms a large proportion of the ethylbenzene into a mixture of xylenes, as described by the Applicant in U.S. Pat. No. 6,369,287. In general, a catalyst based on zeolite (for example of the EUO type) is used, comprising platinum and functioning in the presence of hydrogen;

dealkylating isomerization, frequently using a catalyst comprising ZSM-5 zeolite functioning in the presence of hydrogen, and transforming ethylbenzene into benzene and ethylene to a large or major extent (typically hydrogen to ethane) as described, for example, in U.S. Pat. Nos. 4,163,028; 4,132,790 and 4,899,011. Conventionally, isomerization is defined as dealkylating if more than 30% of the ethylbenzene which is converted is dealkylated to benzene. Usually, 70% transformation is obtained by dealkylation.

b) further, disproportionation (or dismutation) of toluene into xylenes and benzene. Reference may in particular be made to the following patents: U.S. Pat. No. 4,052,476; U.S. Pat. No. 4,007,231; U.S. Pat. No. 4,011,276; and to the article "Selective toluene disproportionation process proven at Italian refinery" Gorra F, Breckenbridge L L, Guy W M, Sailor R A, Oil and Gas Journal V90, 60-67 (1992), concerning the selective disproportionation of toluene to para-xylene by a process known as MSTDP or PX max. Reference may also be made to the following European, United States and International patents: EP-A-0 026 962; U.S. Pat. No. 4,260,843; U.S. Pat. No. 4,274,982; U.S. Pat. No. 4,908,342; U.S. Pat. No. 5,173,461 and WO-A-93/17987.

The invention, which typically employs these two process steps to increase the overall production of para-xylene, may use any of the processes known in the prior art to carry out isomerization and disproportionation, and is not limited to one or more of said processes. However, highly preferably, selective disproportionation of toluene is employed.

Further, dealkylating isomerization may be used, converting isomerization (to xylenes) usually being preferred when the $C_8$ aromatic feed is insufficient as regards quantity.

The two techniques or processes (i.e. separation) for producing para-xylene which are routinely in use, alone or in combination, are simulated moving bed (SMB) adsorption and crystallization.

The first of said well known separation techniques is simulated moving bed adsorption using an absorbent having selective adsorption between para-xylene and the other xylenes. Reference may also be made to the following patents: U.S. Pat. No. 2,985,589 (simulated counter-current) or U.S. Pat. No. 4,402,832 (simulated co-current).

The adsorption facility typically comprises at least one and often 2 chromatographic columns each comprising a plurality of beds which are interconnected in a closed loop. Typically, there are at least two injection points, one for the feed and the other for a desorbant, and at least two withdrawal points, one for the extract E* which is typically rich in PX and the other for a raffinate R* which typically depleted in or free of PX. Said 4 injection/withdrawal points, the positions of which vary sequentially over time, then define 4 functional zones of the adsorption column or columns.

A number of variations are possible, however:

supplemental injection may be used, of a reflux rich in PX;

a 5 or more adsorption zone function may also be used, by not withdrawing a single raffinate R* but 2 raffinates, R1* and R2*. In such a case, the raffinate R1* or intermediate raffinate typically contains ethylbenzene, and the raffinate R2* typically contains ortho-xylene) OX) and meta-xylene (MX), the zone between the withdrawal of R1* and that of R2* then being an ethylbenzene adsorption zone. This operation with two raffinates R1*, R2* has been described in U.S. Pat. No. 6,838,588, U.S. Pat. No. 6,841,714 and U.S. Pat. No. 6,828,470.

These variations, and others which are known in the art, may be employed separately or jointly in the context of the invention, and the invention is not limited to one or more thereof.

The second known separation technique is crystallization, which provides high purity PX crystals and a mother liquor ML comprising relatively low purity PX. The crystallization feed may typically be an effluent from a simulated bed adsorption unit (this is known as hybrid technology) or an effluent from a toluene disproportionation unit. There may be one or two successive crystallization zones or even more, possibly at different temperatures (for example at high temperature ($-25°$ C./$+10°$ C.) and low temperature ($-50°$ C./$-70°$ C.). It may also be possible to carry out partial crystallization of the mother liquor and/or partial remelting of the crystals. Reference may be made in this regard to United States and French patents U.S. Pat. No. 3,177,255; U.S. Pat. No. 3,467,724; FR-A-2 739 375. This latter patent of the Applicant also describes a particular concatenation advantageously used in accordance with the invention, consisting of placing a unit for selective disproportionation of toluene followed by a crystallization unit in parallel with the simulated moving bed separation unit. It may then have a supplemental advantage supplied by recycling the crystallization mother liquor to the feed for the simulated moving bed unit operated with toluene as the desorbant, to dispense with a distillation column.

In one crystallization, there are typically 3 steps: 1) production of crystals (scraped cooling tubes, mixing and depressurization with evaporation of $CO_2$ or propane, dropping film); 2) filtration of crystals in suspension; 3) recovering and washing crystals to eliminate the residual mother liquor. According to the invention, it is possible to use a static crystallizer using the dropping film crystallization technique. This type of equipment can in general divide the amount of impurities of para-xylene by a factor in the range 10 to 15. It is possible to use several modules in parallel and/or in series. When treating xylenes from the selective disproportionation of toluene, the amount of para-xylene feed is typically about 85% by weight. This can then produce, in a first module, para-xylene with a purity which is typically in the range 98.5% to 99%, and in a second module in series, produce a purity of 99.85% to 99.9%. The mother liquor produced in the second module may be recycled to the first module.

Said variations and technologies and others which are known in the prior art (for example crystallizers using filtration and/or centrifuging), may be employed separately or jointly in the context of the invention, and the invention is not bound or limited to one or more thereof.

Said two processes for separating para-xylene from a mixture of aromatic $C_8$ compounds, which are separation by simulated moving bed chromatography and crystallization, may be used either alone or in combination, as described in the Applicant's article entitled "Para-xylene production with the Eluxyl process: Debottlenecking with hybrid Eluxyl" by G Hotier A Methivier, March 2002, Proceedings of the AICHE Conference.

To satisfy the ever increasing demand for para-xylene, petrochemists seek to produce a maximum quantity of para-xylene in existing units by optimizing the conduct of the process. Beyond that, they have the choice between expanding capacity, either by debottlenecking existing units, or by using new very expensive units typically producing at least 300000 tonnes/year and preferably at least 450 000 tonnes/year of PX.

The debottlenecking operations of the prior art typically necessitate modifying the principal elements of existing facilities, in particular the SMB portion, which involves substantial expense.

Another problem exists, frequently encountered by petrochemists, which tends to limit production capacity: this problem results in the need to maintain the simulated moving bed chromatography unit in production for as long as possible with a para-xylene purity of more than 99.7%. When the molecular sieve (absorbent) placed in the simulated moving bed separation unit is new, typical performances of the unit are a purity of the order of 99.85% with a yield of the order of 97.5%. Recent large size units, at iso-productivity and iso-yield, often produce an annual purity loss of 0.025% to 0.1% due to ageing of the absorbent. Certain producers have to change their molecular sieves up to 3 times in 6 years. To be able to continue to operate their unit with the required purity of 99.7%, it was sometimes necessary to let the yield drop below 80%, or to greatly reduce the flow rate of the feed while awaiting the delivery of a fresh batch of new molecular sieve. This problem is not satisfactorily resolved in the prior art, and there is thus a marked interest in a process or a technical solution which would allow the operations to be extended by several months to be able to smooth this out.

BRIEF DESCRIPTION OF THE INVENTION

In a first aspect, the invention provides an improved process for the production of para-xylene for increasing the production of para-xylene, by operating existing units in a different manner.

In a second aspect, the invention provides a process for limiting the drop in production resulting from natural and/or accidental ageing of the absorbent over time.

In a third aspect, the invention is a process for carrying out debottlenecking, in particular by about 20% to 25% of supplemental capacity, with limited modifications to existing units, typically by re-using all of the principal equipment and by adding a limited amount of equipment.

The process of the invention typically uses a production of PX with high purity using, in parallel, simulated moving bed SMB adsorption and crystallization of an effluent from the selective disproportionation of toluene.

One of the essential characteristics of the invention is to substitute, when the function of the SMB degrades due to ageing of the absorbent, a fraction Ea of the distilled extract E to the initial feed for crystallization, to produce a crystallization para-xylene which is practically pure and thus compensates for the drop in purity over time of the SMB extract E, the purity of which may then drop below the required value. The adsorption and crystallization units then operate partially in series (and not totally in series as in the hybrid configuration).

Advantageously, the xylenes from the selective disproportionation, which are rich in PX are then recycled to the SMB, which improves its function and increases its supply flow rate. Crystallization, supplied by a high purity stream, also has an improved function and may operate at a greatly increased flow rate. The adsorption raffinate is typically isomerized then recycled.

The invention allows a high production of PX and benzene to be maintained despite ageing of the absorbent.

The preferred implementation of the invention thus uses four base units: adsorption (SMB), crystallization, isomerization, selective disproportionation. These 4 units are already used in certain petrochemicals complexes.

In certain of said complexes, there already exists a unit for non selective disproportionation of toluene into benzene and xylenes. To transform said unit into a selective disproportionation unit, changing the catalyst generally suffices. This results in a favourable change in the composition of the effluent, which becomes rich in PX.

Conventionally, in accordance with the invention, the term "selective disproportionation" is used when the effluent from disproportionation has a concentration of at least 50% by weight of para-xylene within the $C_8$ disproportionation cut (typically, about 85% is obtained). The selective character (towards PX) essentially depends on the choice of catalyst.

If the complex does not include crystallization, such a unit must also be installed, typically adapted to the flow rate of the fractionated effluent ($C_8$ cut) from selective disproportionation. In all cases, the debottlenecking of the invention does not require a great deal of investment such as installing a new SMB adsorption unit or a substantial modification to the existing SMB unit.

DETAILED DESCRIPTION OF THE INVENTION

The term "operational cycle" of the process as used below designates a period for the production of para-xylene in which the absorbent (adsorption sieve of SMB) is new at the start of the cycle, and where the SMB facility is stopped at the end of the cycle to replace said absorbent, which is then used, with new absorbent. Thus, the absorbent ages continuously between the start and end of a cycle.

The invention proposes a process for the combined production of high purity para-xylene HPPX and benzene from a first feed principally comprising xylenes and ethylbenzene, and from a second feed principally comprising toluene, in a facility comprising at least the following:
- a unit for the selective disproportionation of toluene to benzene and xylenes;
- a unit for para-xylene crystallization;
- a SMB unit for simulated moving bed adsorption, comprising at least one chromatographic column containing a plurality of beds of an absorbent having a different selectivity for para-xylene, ethylbenzene, meta-xylene and ortho-xylene, said column using a desorbant;

in which:
a) during the whole of at least one operational cycle of the process:
- an adsorption feed comprising at least a fraction of said first feed is separated by simulated moving bed adsorption in said simulated moving bed adsorption unit SMB to produce an extract E* which is rich in para-xylene and at least one raffinate (R*, R2*) which is depleted in para-xylene and contains ortho-xylene and meta-xylene;
- said raffinate (R*, R1*, R2*) is distilled to recover a distilled raffinate (R, R1, R2) which is substantially free of desorbant;
- the extract E* is distilled to recover a distilled extract E, substantially free of desorbant;

b) during an initial fraction IF of said operational cycle of the process, high purity para-xylene HPPX is produced comprising substantially all of the distilled extract E, the crystallization unit being, during said initial fraction IF, either stopped or essentially supplied with at least a portion of a $C_8$ disproportionation stream essentially comprising xylenes and more than 50% by weight of para-xylene, derived from effluents from conversion of said second feed in said selective disproportionation unit;

c) during a final fraction FF of said operational cycle of the process;
- said second feed is converted in the unit for selective disproportionation of toluene to benzene and xylenes, to produce benzene and a $C_8$ disproportionation stream essentially comprising xylenes and more than 50% by weight of para-xylene;
- the largest portion or all of said $C_8$ disproportionation stream is integrated into the adsorption feed;
- the distilled extract E is divided into a first fraction Ea and a complementary second fraction Eb;
- then the crystallization unit is essentially supplied with Ea to produce enhanced purity para-xylene PX1 and a mother liquor ML;
- and the PX1 and said complementary second fraction Eb are mixed to produce high purity para-xylene HPPX.

Typically, the final fraction of the operational cycle of the process is the part of the cycle which is complementary to the initial fraction of the operational cycle.

Generally, during the initial fraction IF of the operational cycle, the high purity para-xylene HPPX produced is constituted by all of the distilled extract E. This para-xylene is then typically of the required purity, most generally at least 99.7%, for example at least 99.8%.

When the purity of E reduces and tends towards the acceptable limit due to ageing of the absorbent, a fraction Ea of the stream E is sent to the crystallization step. Since the crystallization feed is already very pure (typically in the range 99.4% to 99.7%), the crystallized para-xylene obtained is practically pure (more than 99.8% and typically more than 99.9%) and can compensate for the lack in purity of the stream Eb integrated directly into HPPX. Ea typically represents between 10% and 70% and generally between 15% and 45% by weight of E.

Typically, during said final fraction FF of the operational cycle, the purity of PX1 is at least 99.8%, that of Ea and Eb is less than 99.7% and that of HPPX is at least 99.7%.

In accordance with a first characteristic variation of the process, during the initial fraction IF of the operating cycle, the crystallization unit is supplied with a crystallization feed constituted by at least part or all of the $C_8$ disproportionation stream. The crystallization unit is then in service, supplied with $C_8$ disproportionation compounds with a para-xylene concentration which is typically close to 85% by weight. It produces para-xylene PX1 with a typical concentration of at least 99.7%, which is supplemented with the distilled extract E to constitute the high purity para-xylene HPPX. When swung into the final operational mode (FF), the crystallization feed (disproportionation $C_8$, with a typical concentration of close to 85% by weight of PX) is typically swung to the simulated moving bed adsorption SMB. This enriches the SMB feed in PX, which improves its operation (yield and/or purity).

In a second characteristic variation of the process, during the initial fraction IF of the operational cycle, the crystallization unit is not in service. This variation is advantageously employed when there is an excess of benzene on the market or when the mediocre upgrade of benzene does not by itself justify the cumulative operational costs of disproportionation and crystallization. The situation is modified at the end of the cycle as the supply of disproportionation $C_8$, typically with a high concentration of PX (eg 85%) enriches the SMB feed in PX and thus can produce more PX and/or improve its purity at the outlet from the SMB.

In general, the operation of the disproportionation/crystallization assembly can produce both benzene and produce supplemental para-xylene and/or para-xylene with a higher purity, which means that the cycle period can be extended, maintaining a given production.

Typically, the flow rate of the crystallization feed is much higher during the final fraction FF of the cycle than during the initial fraction IF of the cycle. This flow rate of the crystallization feed is typically increased by at least 50%, or may even be doubled or more during the final fraction FF of the cycle compared with the initial fraction IF of the cycle. This results from the very high purity of the crystallization feed. It can in particular allow operation with two stages of crystallization in parallel instead of two stages in series. Further, partial remelting of the crystallized PX can often be avoided, as it is already of very high purity, which saves operating time and thus increases capacity.

Advantageously, at least a portion or generally all of the mother liquor ML is recycled to the adsorption feed, which allows more PX to be recovered.

Generally, the facility for carrying out the process, which constitutes a further aspect of the invention, also comprises at least one isomerization unit supplied with distilled reagent (R, R1, R2), and at least a portion of the isomerization effluent (from its $C_8$ fraction) is recycled and integrated into the adsorption feed.

In accordance with a further characteristic of the invention, the chromatographic column (or SMB unit with 2 columns) produces a first raffinate R1* comprising ethylbenzene, ortho-xyiene and meta-xylene, and a second raffinate R2* which is substantially free of ethylbenzene and comprising ortho-xylene and meta-xylene, the first raffinate R1, after distillation to substantially eliminate the desorbant it contains, is supplied to a first isomerization unit in the gas phase to convert at least a portion of the ethylbenzene to benzene and/or xylenes, the second raffinate R2, after distillation to substantially eliminate the desorbant it contains, is supplied to a second isomerization unit in the liquid phase, and at least a portion of each of the isomerization effluents is recycled to the adsorption feed.

The use of a dealkylating isomerization is thus more general (with 1 or 2 raffinates). The distilled raffinate (R, R1) is thus supplied to a dealkylating isomerization unit to convert at least a portion of the ethylbenzene to benzene, and the unit then produces benzene part of which derives from the toluene disproportionation unit and the other part of which derives from the dealkylating isomerization unit.

When using two raffinates and two isomerization units, the first isomerization unit (R1), in the gas phase, is usually a dealkylating isomerization unit to convert at least a portion of the ethylbenzene to benzene, and the second isomerization unit (R2), in the liquid phase, is typically a converting and non dealkylating isomerization unit to convert at least the major portion of the ortho-xylene and para-xylene into a mixture of xylenes comprising PX (typically close to thermodynamic equilibrium), and benzene is produced a portion of which derives from the toluene disproportionation unit and the other portion of which derives from the dealkylating isomerization unit. The second isomelization unit liquid phase can thus increase the quantity of para-xylene. When said PX production is maximized, the first isomerization unit may also be converting and non dealkylating.

Typically, the isomerization effluents are not recycled to the adsorption unit in their entirety. Generally, the various fractions of the essentially aromatic isomerate (in particular benzene and light compounds comprising propane, butane) are separated by distillation and only the essentially $C_8$ aromatic cut is recycled.

Frequently, the first feed is initially distilled in a xylene distillation column, from which an overhead fraction is withdrawn which comprises the major portion of the meta-xylene, para-xylene, ethylbenzene and at least a portion of the ortho-xylene, which overhead fraction is integrated into the adsorption feed, and a bottom fraction comprising $C_9$-$C_{10}$ hydrocarbons and/or the remaining part of the ortho-xylene.

Figure 1:
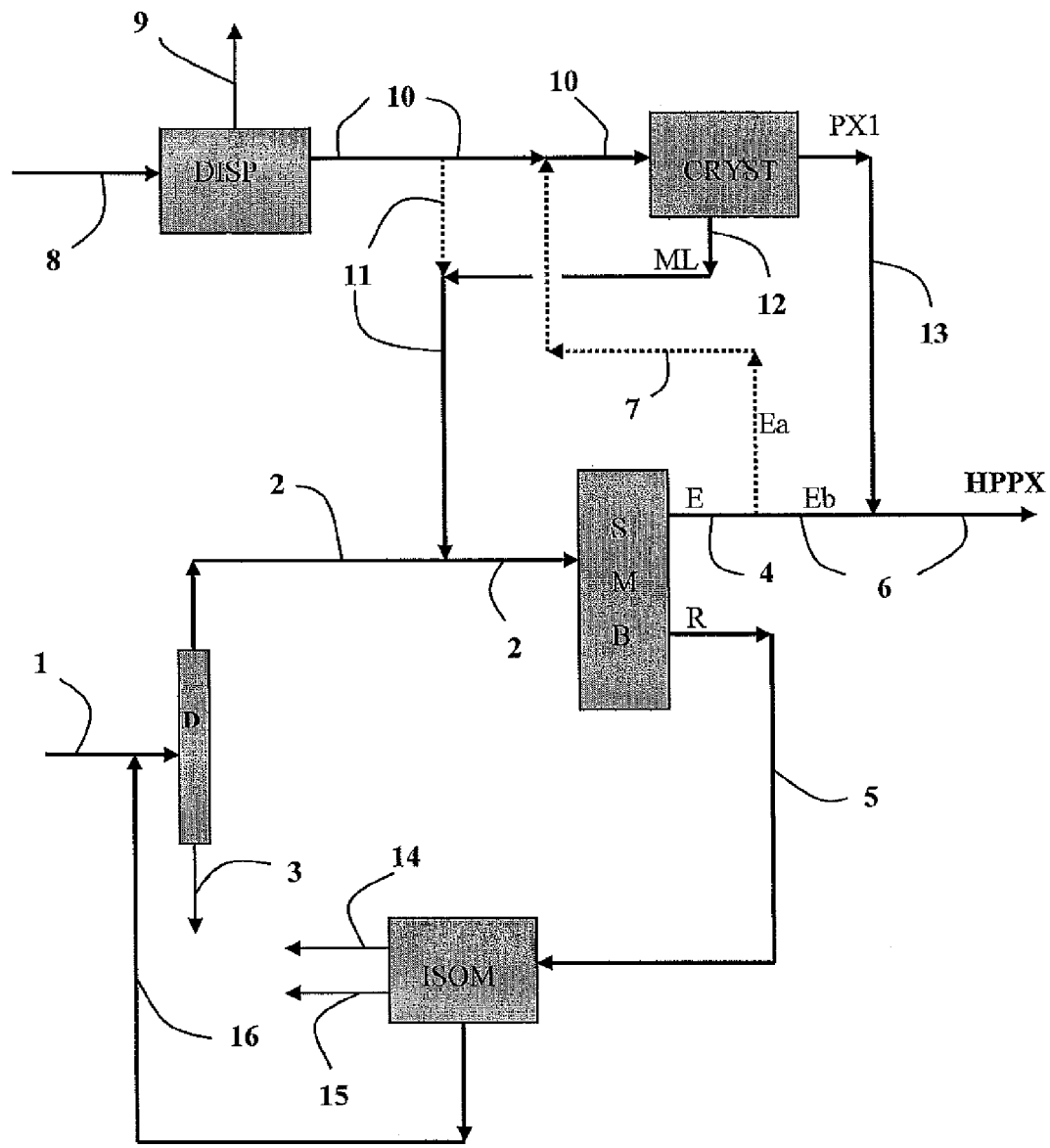
FIG. 1 shows a simplified flow chart for a facility for carrying out the process of the invention showing the typical movement of the various streams at the start of the production cycle (movement mode "sieve life start" during the fraction IF of the cycle).

Reference should now be made to FIG. 1 (start of cycle):

The flow chart of FIG. 1 shows an initial distillation (D) of the feed, a unit (SMB) for simulated moving bed adsorption, an isomerization unit (ISOM), a unit (DISP) for selective disproportionation of toluene, and a unit (CRYST) for para-xylene crystallization PX.

The first aromatic feed, comprising xylenes and typically a minor $C_9$/$C_{10}$ fraction, enters via a line 1 into the distillation (D). It is mixed with an isomerate moving in a line 16, then fractionated into an overhead cut leaving via a line 2, comprising the major portion of the PX, MX, ethylbenzene EB, and at least a portion of the OX. A stream of $C_9$/$C_{10}$ hydrocarbons leaves the column bottom via a line 3 and the remaining portion of OX. The overhead cut, supplemented with streams from a line 1 supplies the simulated moving bed adsorption (SMB), typically as a simulated counter-current and at least 4 adsorption zones. The desorbant used (the inlet thereof into the SMB is not shown) may be toluene or para-diethylbenzene, or any other selective solvent. An extract E* leaves the SMB unit, which is distilled (not shown) to eliminate the solvent which is recycled, and to produce a distilled extract E via a line 4. A raffinate r* also leaves and is distilled (also not shown) to eliminate the solvent, which is recycled, and to produce a distilled raffinate R via a line 5.

At the start of the cycle, the distilled extract E typically moves in its entirety in a line 6 (E=Eb, Ea=0; and the line 7 is empty). When the absorbent is new, said extract E generally has, a purity of 99.85% and is obtained in a yield of 97%. E is then mixed with the crystallization effluent PX1 (crystallized para-xylene, separated from the mother liquor ML, typically washed and re-melted, with a typical purity of 99.7% to 99.8%) moving in a line 13. High purity para-xylene, HPPX, is then obtained. It is also possible to operate by increasing the SMB flow rate to produce an increased quantity of PX (extract E) with a purity which is just satisfactory, for example between 99.7% and 99.75%.

The distilled reagent R, containing OX, MX and EB, supplies the isomerization, typically dealkylating (ISOM) via line 5, producing, after distillation, a small quantity of incondensable light products via a line 14 and benzene via a line 15. Toluene may also be evacuated as a mixture via line 15 or by a separate line, not shown. $C_8$ compounds containing para-xylene (isomerate) are recycled to the inlet to column D via a line 16. Frequently, said recycle of isomerate undergoes a prior earth treatment, not shown, to remove traces of olefins which are present.

A toluene feed is also supplied to the unit (DISP) for selective disproportionation of toluene to benzene and xylenes (principally PX) via a line 8. After distillation (several columns) of effluents, the unreacted toluene is recycled (via a line which is not shown), the benzene is evacuated via a line 9, and a $C_8$ cut, rich in PX (about 85% by weight) is transferred to the crystallization unit (CRYST) via a line 10. Said unit produces high purity PX (sufficient purity, for example between 99.7% and 99.85%) and a mother liquor ML which is recycled to the unit (SMB) via lines 12 then 11.

As shown in FIG. 1, the facility produces, at the start of the cycle (fresh absorbent with maximum efficiency), high purity PX, HPPX, in maximum quantity and/or purity deriving in parallel firstly from the unit (SMB) the purity of the distilled extract of which then typically exceeds or is close to 99.7%, and secondly from the crystallization unit. The flow rate of PX1 compared with that of E is thus usually in the range 8% to 40% and preferably between 10% to 25% of E.

Figure 2:
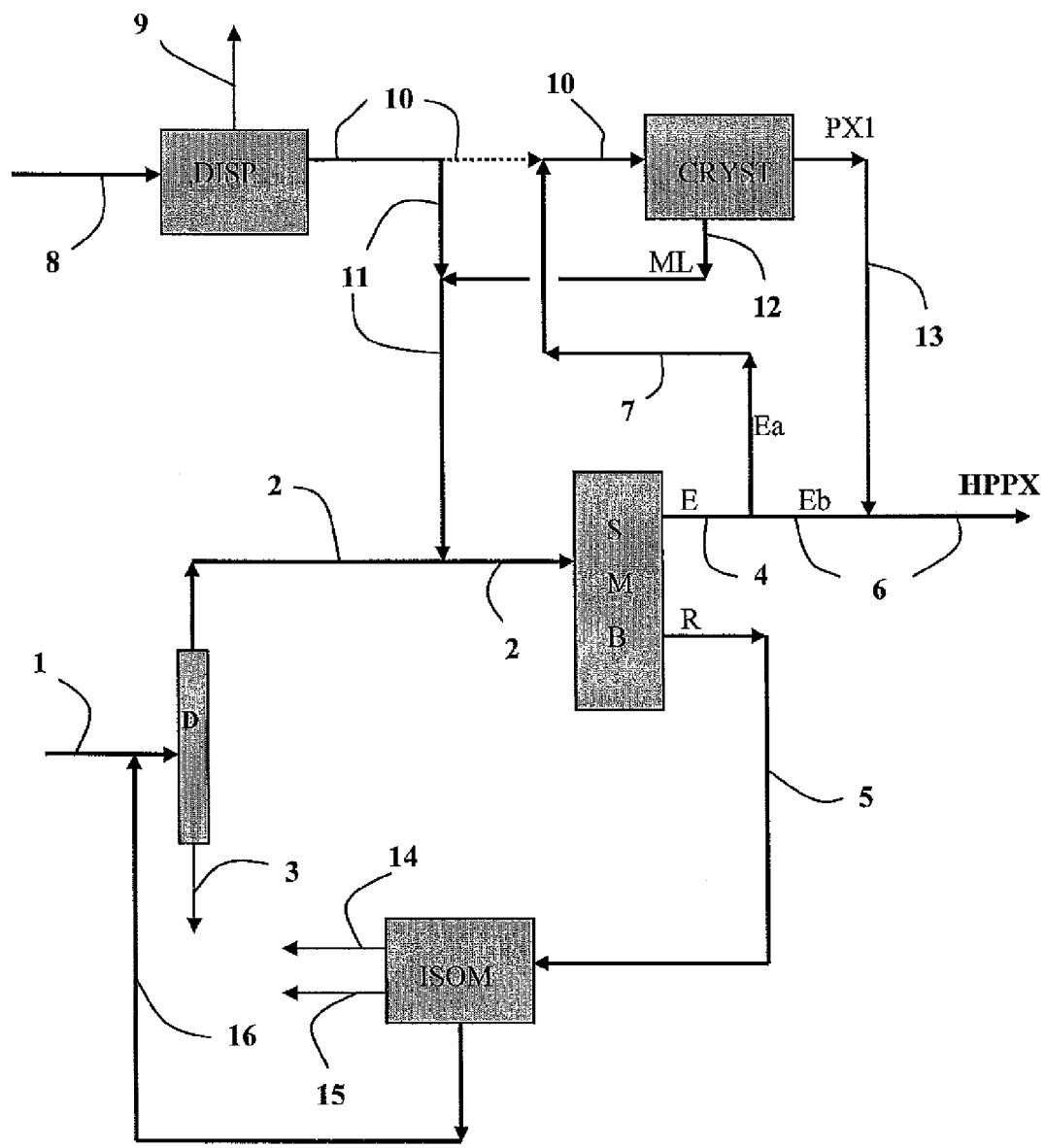
FIG. 2 shows a simplified flow chart for a facility for carrying out the process of the invention showing the typical movement of the various streams at the end of the production cycle (movement mode ("sieve life end" during the fraction FF of the cycle).

FIG. 2 represents the typical circulation of the various streams at the end of the cycle, when the absorbent is old and has limited efficiency and/or selectivity, resulting in a (limited) drop in the purity of E below 99.7% by weight, for example between about 99.45% and 99.7% by weight. In this case, the stream E is divided into a stream Ea which is recycled to the crystallization (CRYST) via line 7, and a complementary stream Eb which continues to form a BPPX fraction, but in smaller proportions than at the start of the cycle.

Because of the very high purity of the crystallization feed, the flow rate of said feed may be greatly increased, and the purity of PX1 may be very high, for example between 99.9% and 99.99%, with a high yield. Superior purity para-xylene (PX1) is thus produced, which compensates for the drop in purity of Eb, directly integrated into HPPX and with a purity which remains at least 99.7%. To minimize the consumption of the crystallization chillers, Ea may be steadily increased at the end of the cycle, to ensure a flow rate Ea which is just sufficient for the purity of HPPX to be just that required (for example 99.7%).

The invention can thus maintain a target purity without having to stop the SMB unit, including when the purity of the extract from said unit drops below the target value.

Because Ea is sent to the crystallization feed, part or all of the $C_8$ disproportionation effluent is returned to the adsorption step (SMB) via a line 11. The SMB feed thus has an increased concentration of PX, improving the productivity and/or purity of the distilled extract E. This can also increase the SMB supply flow rate.

Thus, the invention can produce maximum amounts of very high purity product at the end of the cycle without having to substantially reduce the production of HPPX.

By dint of limited modification to existing units, such as a change in the disproportionation catalyst and/or adding a crystallization step, the invention can substantially debottleneck existing facilities which do not have such units, without having to modify or double up on the most expensive unit (SMB).

A number of variations may be employed by the skilled person without departing from the scope of the invention. In particular, a unit (SMB) may be used with two raffinates R1* and R2* instead of one, and/or a non alkylating isomerization unit for ethylbenzene and/or various configurations for the crystallization units, etc.

The scope of the invention also includes employing an operation with minor differences such as: at the beginning of the cycle (IF), sending a minor fraction of the extract to the crystallization (mixed with the principal feed of selective disproportionation xylenes) or at the end of the cycle sending a minor fraction of selective disproportionation xylenes to the crystallization step (mixed with the principal feed Ea).

EXAMPLES

Example 1

In Accordance with the Prior Art

The facility in the process of Example 1 corresponds to that indicated in FIG. 1, and comprises a SMB unit with a single raffinate and a dealkylation isomerization. However, the lines shown as dotted lines in said figure (line 7 and the first portion of line 11) are not included in this facility.

The flow chart remains the same, between the start and end of the cycle, but with a flow rate of the first feed which reduces and a PX production leaving the SMB which substantially reduces at the end of the cycle to be able to maintain the required minimum purity (99.7%) for para-xylene. The yield of SMB also falls, along with the benzene production.

Table 1 shows a material balance (in tonnes per hour) for the various streams referred to in FIG. 1 at the start of the cycle (fresh absorbent) and Table 2 shows the same material balance, bat at the end of the cycle (used absorbent, just before its replacement). The following abbreviations are used: PX=para-xylene; OX=ortho-xylene; MX=meta-xylene; EB=ethylbenzene; T=toluene; BZ=benzene; LPG=$C_4$/$C_3$, and possibly small quantities of $C_2$ and $C_1$.

TABLE 1

| Start of cycle | Feed 1 | SMB inlet | R | E | Ea | Feed 2 | Outlet DISP | Inlet CRYST | PX1 | ML | HPPX | Outlet ISOM |
|---|---|---|---|---|---|---|---|---|---|---|---|---|
| EB | 17 | 22.4 | 22.4 | — | — | — | — | — | — | — | — | 5.4 |
| PX | 19.6 | 90.8 | 2.7 | 88.1 | — | — | 17 | 17 | 11.9 | 5.1 | 100 | 66.1 |
| MX | 40 | 177 | 177 | — | — | — | 2 | 2 | — | 2 | — | 135 |
| OX | 20.4 | 90.2 | 90.2 | — | — | — | 1 | 1 | — | 1 | — | 68.8 |
| T | — | — | — | — | — | 42 | —(*) | — | — | — | — | — |
| BZ | — | — | — | — | — | — | 20 | — | — | — | — | 12.4 |
| LPG and losses | — | — | — | — | — | — | 2 | — | — | — | — | 4.6 |
| Total | 97 | 380.4 | 292.3 | 88.1 | 0 | 42 | 42 | 20 | 11.9 | 8.1 | 100 | 292.3 |

(*)After recycling unconverted toluene. The conversion per pass is typically 30%. The purity of the distilled extract E is 99.85% at the start of the cycle, with a high yield (at the SMB) of 97%.

TABLE 2

| End of cycle | Feed 1 | SMB inlet | R | E | Ea | Feed 2 | Outlet DISP | Inlet CRYST | PX1 | ML | HPPX | Outlet ISOM |
|---|---|---|---|---|---|---|---|---|---|---|---|---|
| EB | 13.6 | 17.89 | 17.89 | — | — | — | — | — | — | — | — | 4.29 |
| PX | 15.68 | 78.37 | 6.27 | 72.1 | — | — | 17 | 17 | 11.9 | 5.1 | 84 | 57.59 |
| MX | 32 | 151.53 | 151.53 | — | — | — | 2 | 2 | — | 2 | — | 117.53 |
| OX | 16.32 | 77.26 | 77.26 | — | — | — | 1 | 1 | — | 1 | — | 59.94 |
| T | — | — | — | — | — | 42 | —(*) | — | — | — | — | — |

TABLE 2-continued

| End of cycle | Feed 1 | SMB inlet | R | E | Ea | Feed 2 | Outlet DISP | Inlet CRYST | PX1 | ML | HPPX | Outlet ISOM |
|---|---|---|---|---|---|---|---|---|---|---|---|---|
| BZ | — | — | — | — | — | — | 20 | — | — | — | — | 9.88 |
| LPG and losses | — | — | — | — | — | — | 2 | — | — | — | — | 3.72 |
| Total | 77.6 | 325.05 | 252.95 | 72.1 | 0 | 42 | 42 | 20 | 11.9 | 8.1 | 84 | 292.3 |

It can be seen that at the end of the cycle, due to ageing of the absorbent, the rate of supply of the first feed (and thus the overhead cut from column D) has had to be reduced by about 20% to maintain a minimum purity of the extract of 99.7%. In parallel, the PX yield from the SMB has dropped, moving from 97% to 92%. This results in a drop in overall production (HPPX) of 16%, which is a big drop. Further, the reduction in feed causes a drop in the overall production of benzene by about 8%.

Example 2

In Accordance with the Invention

The operation at the start of the cycle is identical to that of the prior art. In contrast, at the end of the cycle (for example once the purity of the refined extract E approaches 99.7%, at constant flow rates for the first and second feeds), the supply to the crystallization step is replaced by a fraction Ea of E, and the $C_8$ disproportionation cut is sent to the SMB supply, which improves its operation because of its enrichment in PX of the overall feed from the SMB. The SMB supply flow rate may thus be increased, and the material balance is thus as follows:

TABLE 3

| End of cycle | Feed 1 | SMB inlet | R | E | Ea | Feed 2 | Outlet DISP | Inlet CRYST | PX1 | ML | HPPX | Outlet ISOM |
|---|---|---|---|---|---|---|---|---|---|---|---|---|
| EB | 17 | 22.4 | 22.3 | 0.08 | 0.03 | — | — | 0.03 | — | 0.03 | 0.05 | 5.4 |
| PX | 19.6 | 106.8 | 3.2 | 103.64 | 39.86 | — | 17 | 39.86 | 36.01 | 3.85 | 99.78 | 66.4 |
| MX | 40 | 177.6 | 177.4 | 0.22 | 0.09 | — | 2 | 0.09 | — | 0.08 | 0.15 | 135.5 |
| OX | 20.4 | 90.55 | 90.4 | 0.11 | 0.04 | — | 1 | 0.04 | 0.01 | 0.04 | 0.07 | 69.1 |
| T | — | — | — | — | — | 42 | —(*) | — | — | — | — | — |
| BZ | — | — | — | — | — | — | 20 | — | — | — | — | 12.3 |
| LPG and losses | — | — | — | — | — | — | 2 | — | — | — | — | 4.6 |
| Total | 97 | 397.35 | 293.3 | 104.05 | 40.02 | 42 | 42 | 40.02 | 36.02 | 4 | 100.05 | 293.3 |

It can thus be seen that the invention can maintain an identical production at the end of the cycle, with no losses of para-xylene nor of benzene. This constitutes a major advantage over the prior art. The purity of para-xylene HPPX, which was more than 99.7% at the start of the cycle, has dropped back to the required value of 99.7% at the end of the cycle.

The invention claimed is:

1. A process for the combined production of high purity para-xylene HPPX and benzene from a first feed principally comprising xylenes and ethylbenzene, and from a second feed principally comprising toluene, in a facility comprising at least the following:

a unit for the selective disproportionation of toluene to benzene and xylenes;
a unit for para-xylene crystallization;
a SMB unit for simulated moving bed adsorption, comprising at least one chromatographic column containing a plurality of beds of an absorbent having a different selectivity for para-xylene, ethylbenzene, meta-xylene and ortho-xylene, said column using a desorbant;

in which:

a) during the whole of at least one operational cycle of the process:
an adsorption feed comprising at least a fraction of said first feed is separated by simulated moving bed adsorption in said simulated moving bed adsorption unit SMB to produce an extract E* which is rich in para-xylene and at least one raffinate which is depleted in para-xylene and contains ortho-xylene and meta-xylene;
said raffinate is distilled to recover a distilled raffinate (R) which is substantially free of desorbant;
the extract E* is distilled to recover a distilled extract E, substantially free of desorbant;

b) during an initial fraction IF of said operational cycle of the process, high purity para-xylene HPPX is produced comprising substantially all of the distilled extract E, the crystallization unit being, during said initial fraction IF, either stopped or essentially supplied with at least a portion of a C8 disproportionation stream essentially comprising xylenes and more than 50% by weight of para-xylene, derived from effluents from conversion of said second feed in said selective disproportionation unit;

c) during a final fraction FF of said operational cycle of the process;
said second feed is converted in the unit for selective disproportionation of toluene to benzene and xylenes, to produce benzene and a C8 disproportionation stream essentially comprising xylenes and more than 50% by weight of para-xylene;
the largest portion or all or said C8 disproportionation stream is integrated into the adsorption feed;
the distilled extract E is divided into a first fraction Ea and a complementary second fraction Eb;
the crystallization unit is essentially supplied with Ea to produce higher purity para-xylene PX1 and a mother liquor ML;

and the PX1 and said complementary second fraction Eb are mixed to produce high purity para-xylene HPPX.

2. A process according to claim 1, in which said final fraction of said operational cycle of the process is the part of the cycle which is complementary to the initial fraction of the operational cycle.

3. A process according to claim 1, in which during the initial fraction IF of said operational cycle, the high purity para-xylene HPPX produced is constituted by all of the distilled extract E.

4. A process according to claim 1, in which Ea represents between 20% and 70% of E.

5. A process according to claim 1 in which, during the initial fraction IF of said operating cycle, the crystallization unit is supplied with a crystallization feed constituted by at least part or all of the C8 disproportionation stream.

6. A process according to claim 1, in which during said initial fraction IF of the operational cycle, the crystallization unit is not in service.

7. A process according to claim 1 in which, during said final fraction FF of said operational cycle, the purity of PX1 is at least 99.8%, that of Ea and Eb is less than 99.7% and that of HPPX is at least 99.7%.

8. A process according to claim 1, in which the flow rate of the crystallization feed is substantially higher during the final fraction FF of the cycle than during the initial fraction IF of the cycle.

9. A process according to claim 8, in which the flow rate of the crystallization feed is at least doubled during the final fraction FF of the cycle compared with the initial fraction IF of the cycle.

10. A process according to claim 1, in which at least a part or all of the mother liquor ML is recycled to the adsorption feed.

11. A process according to claim 1, in which said distilled raffinate is supplied to an isomerization unit and at least a portion of said isomerization effluent is recycled and integrated into the adsorption feed.

12. A process according to claim 11, in which the chromatographic column produces a first raffinate R1* comprising ethylbenzene, and a second raffinate R2* which is substantially free of ethylbenzene and comprises ortho-xylene and meta-xylene, and in which the first raffinate R1, after distillation to substantially eliminate the desorbant it contains, is supplied to a first isomerization unit in the gas phase to convert at least a portion of the ethylbenzene to benzene and/or xylenes and the second raffinate R2, after distillation to substantially eliminate the desorbant it contains, is supplied to a second isomerization unit in the liquid phase, and at least a portion of each of the isomerization effluents is recycled to the adsorption feed.

13. A process according to claim 11, in which said distilled raffinate: R or R1 is supplied to a dealkylating isomerization unit to convert at least a portion of the ethylbenzene to benzene, and benzene is produced a portion of which derives from the toluene disproportionation unit and a portion derives from said dealkylating isomerization unit.

14. A process according to claim 12, in which said first isomerization unit, in the gas phase, is a dealkylating isomerization unit to convert at least a portion of the ethylbenzene to benzene, and said second isomerization unit, in the liquid phase, is a converting and non dealkylating isomerization unit to convert at least the major portion of the ortho-xylene and para-xylene into a mixture of xylenes comprising PX, and benzene is produced a portion of which derives from the toluene disproportionation unit and a portion of which derives from the dealkylating isomerization unit.

15. A process according to claim 1, in which the first feed is initially distilled in a xylene distillation column, from which an overhead fraction comprising the major portion of meta-xylene, para-xylene, ethylbenzene and at least a portion of the ortho-xylene is withdrawn, which overhead fraction is integrated into the adsorption feed, and a bottom fraction is withdrawn comprising C9-C10 hydrocarbons and/or the remaining portion of the ortho-xylene.

* * * * *